United States Patent
Meyer et al.

(10) Patent No.: US 8,633,203 B2
(45) Date of Patent: Jan. 21, 2014

(54) USE OF PTEROCARPANS AS ACTIVE ANTI-CELLULITE INGREDIENTS

(75) Inventors: Imke Meyer, Bodenwerder (DE); Oskar Koch, Göttingen (DE); Nadine Hillebrand, Steinheim (DE); Martina Herrmann, Hameln (DE); Holger Joppe, Dassel (DE)

(73) Assignee: Symrise AG, Holzminden (DE)

( * ) Notice: Subject to any disclaimer, the term of this patent is extended or adjusted under 35 U.S.C. 154(b) by 397 days.

(21) Appl. No.: 12/849,600

(22) Filed: Aug. 3, 2010

(65) Prior Publication Data

US 2011/0034486 A1 Feb. 10, 2011

Related U.S. Application Data

(60) Provisional application No. 61/231,473, filed on Aug. 5, 2009.

(51) Int. Cl.
*A61K 31/522* (2006.01)
*A61K 31/35* (2006.01)
*C07D 311/78* (2006.01)
*C07D 311/94* (2006.01)

(52) U.S. Cl.
USPC ............. 514/263.31; 514/453; 549/383

(58) Field of Classification Search
USPC .............. 514/263.31, 453; 549/383
See application file for complete search history.

(56) References Cited

U.S. PATENT DOCUMENTS

| 4,150,052 A | 4/1979 | Watson et al. |
| 4,251,195 A | 2/1981 | Suzuki et al. |
| 4,704,400 A | 11/1987 | Miller et al. |
| 5,721,371 A | 2/1998 | Larock |
| 5,929,124 A | 7/1999 | Hostettmann et al. |
| 6,214,376 B1 | 4/2001 | Gennadios |
| 2006/0089413 A1 | 4/2006 | Schmaus et al. |
| 2008/0070825 A1 | 3/2008 | Bertram et al. |

FOREIGN PATENT DOCUMENTS

| DE | 100 09 423 A1 | 9/2001 |
| DE | 10 2004 032 837 A1 | 2/2006 |
| EP | WO-0389700 A1 | 10/1990 |
| EP | 1 234 572 A1 | 8/2002 |
| JP | 2002053421 A | 2/2002 |
| WO | WO-0176572 A2 | 10/2001 |
| WO | WO-02/15686 A1 | 2/2002 |
| WO | WO-02069992 A1 | 9/2002 |
| WO | WO-03055587 A1 | 7/2003 |
| WO | WO-2004026840 A1 | 4/2004 |
| WO | WO-2004050069 A1 | 6/2004 |
| WO | WO-2005/049553 A1 | 6/2005 |
| WO | WO-2005107692 A1 | 11/2005 |
| WO | WO-2005123101 A1 | 12/2005 |
| WO | WO-2006015954 A1 | 2/2006 |
| WO | WO-2006045760 A1 | 5/2006 |
| WO | WO-2006053912 A1 | 5/2006 |
| WO | WO-2007042472 A1 | 4/2007 |
| WO | WO-2007/060256 A2 | 5/2007 |
| WO | WO-2007110415 A2 | 10/2007 |
| WO | WO-2007/128723 A1 | 11/2007 |
| WO | WO 2007/128725 | * 11/2007 |
| WO | WO-2007/128725 A1 | 11/2007 |
| WO | WO-2008046676 A1 | 4/2008 |
| WO | WO-2008046791 A1 | 4/2008 |
| WO | WO-2008046795 A1 | 4/2008 |

OTHER PUBLICATIONS

Harper et al. (J. Chem. Soc. (C), 1969; p. 1109-1116.*
Cocker et al. (J. Chem. Soc., 1962; p. 4906-4909).*
Chul Lee (Clinica Chimica Acta (2000), 295 (1-2);p. 141-154).*
Rijinkels et al. (Radiat Res. Feb. 2003; 159(2):210-217-Abstract only).*
Lu et al. (Carcinogenesis 2005. 26 (8); p. 1465-1472).*
Fin Sandberg ("The saponin of Swartzia madagascariensis": Pharmaceutisch weekblad, 93 (1958); p. 5-7).*
Carmen, et al., "Signalling mechanisms regulating lipolysis," Cellular Signalling, vol. 18, 2005, pp. 1-8.

(Continued)

*Primary Examiner* — Noble Jarrell
*Assistant Examiner* — Valerie Rodriguez-Garcia
(74) *Attorney, Agent, or Firm* — Novak Druce Connolly Bove + Quigg LLP

(57) ABSTRACT

The invention relates to a cosmetic, dermatological or pharmaceutical preparation, containing one, two or more compounds of formula (I) and/or a pharmaceutically acceptable salt of a compound of this type,

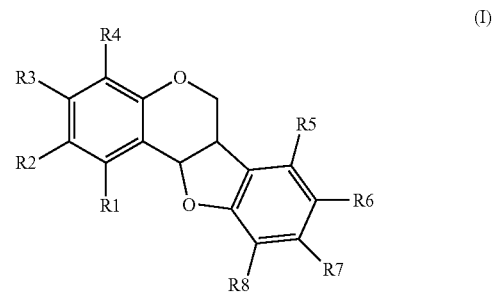

(i) for use in a method for preventing, treating or reducing cellulite, and/or
(ii) in an adequate quantity
  to reduce the lipid quantity contained in subcutaneous fat tissue, and/or
  to inhibit the differentiation of preadipocytes, and/or
  to inhibit the lipogenesis in adipocytes,
wherein the radicals R1 to R8, independently of one another, signify hydrogen, hydroxy or C1-C4-alkoxy, and/or two adjacent radicals together form a methylenedioxy group.

8 Claims, 1 Drawing Sheet

(56) References Cited

OTHER PUBLICATIONS

Kuppusamy et al., "Effects of Flavonoids on Cyclic Amp Phosphodiesterase and Lipid Mobilization in Rat Adipocytes," Biochemical Pharmacology, vol. 44, No. 7, 1992, pp. 1307-1315.

Warnke et al., "Use of Native and Derivatized Cylclodextrin Based and Macrocyclic Glycopeptide Based Chiral Stationary Phases for the Enantioseparation of Pterocarpans by HPLC," Journal of Liquid Chromatography & Related Technologies®, vol. 28, 2005, pp. 823-834.

Aardt et al., "Direct Synthesis of Pterocarpans via Aldol Condensation of Phenylacetates with Benzaldehydes," Tetrahedron, vol. 55, 1999, pp. 11773-11786.

Miki et al., "Reaction of Chalcone with Phenyliodine (III) Bis (trifluoroacetate) (PIFA): Synthesis of (±)-Homopterocarpin," Synlett, J. Chem. Soc., 1994, pp. 1001-1002.

Miki et al., "Oxidative rearrangement of pentaalkoxychalcones with phenyliodine(III) bis(trifluoroacetate) (PIFA): synthesis of (±)-10-bromo-pterocarpin and (±)-pterocarpin," J. Chem. Soc., Perkin Trans. vol. 1, 1998, pp. 2533-2536.

Khupse et al., "Practical Synthesis of Lespedezol $A_1$," J. Nat. Prod., vol. 71, 2008, pp. 275-277.

Kirkbride et al., "Bobgunnia, a new African genus of tribe Swartzieae (Fabaceae, Faboideae)," Brittonia, vol. 49, No. 1, 1997, pp. 1-23.

Hans Dieter Neuwinger: Afrikanische Arzneipflanzen and Jagdgifte, Chemie, Pharmakologie, Toxikologie, Wiss. Verl.-Ges. 1998, pp. 316-321.

Borel et al., "64. Molluscicidal Saponins from Swartzia madagascariensis Desvaux," Helvetica Chimica Acta, vol. 70, 1987, pp. 570-576.

Suter et al., "Laboratory and field trials at Ifakara (Kilombero District, Tanzania) on the plant molluscicide Swartzia madagascariensis," Acta Tropica, vol. 43, 1986, pp. 69-83.

Georges et al., "Pest-managing activities of plant extracts and anthraquinones from Cassia nigricans from Burkina Faso," Bioresource Technology, vol. 99, 2008, pp. 2037-2045.

Ahua et al., "Antileishmanial activities associated with plants used in the Malian traditional medicine," Journal of Ethnophramacology, vol. 110, 2007, pp. 99-104.

Koné et al., "Traditional medicine in North Côte-d' Ivoire: screening of 50 medicinal plants for antibacterial activity," Journal of Ethnopharmacology, vol. 93, 2004, pp. 43-49.

Magassouba et al., "Ethnobotanical survey and antibacterial activity of some plants used in Guinean traditional medicine," Journal of Ethnopharmacology, vol. 114, 2007, pp. 44-53.

Harper et al., "Pterocarpanoid Constituents of the Heartwoods of Pericopsis angolensis and Swartzia madagascariensis," J. Chem. Soc., 1969, pp. 1109-1116.

Carpéné et al., "Selective activation of $\beta_3$-adrenoceptors by octopamine: comparative studies in mammalian fat cells," Naunyn-Schmiedeberg's Arch Pharmacol, vol. 359, pp. 310-321, (1999).

* cited by examiner

USE OF PTEROCARPANS AS ACTIVE ANTI-CELLULITE INGREDIENTS

CROSS-REFERENCE TO RELATED APPLICATIONS

This application claims priority under 35 U.S.C. §119(e) to U.S. provisional application No. 61/231,473, filed Aug. 5, 2009, the entire contents of which are hereby incorporated by reference.

The present invention primarily relates to the use of certain pterocarpans of formula (I) given below as active anti-cellulite ingredients, (cosmetic) preparations, which are suitable for the prophylaxis and cosmetic treatment of cellulite in people, and corresponding cosmetic methods.

Cellulite is also known under the synonyms protrusio cutis and colloquially as orange peel skin. It is a cosmetic-aesthetic problem which is accompanied by the formation of dimples and indentations of the skin and nodule formation of the subcutaneous fat tissue. Cellulite can occur at any point of the human body, but the outer side and the back of the thighs as well as the buttocks are most frequently affected. Breasts, lower stomach, upper arms or neck are also sometimes affected by cellulite. Cellulitis is to be clearly separated and distinguished from the cosmetic phenomenon of cellulite. Cellulitis is a bacterial infection of the subcutaneous fascia tissue, which in many cases may be a serious illness, and in contrast to cellulite, has to be treated therapeutically.

Cellulite may be regularly found on points of the human body with excessive fat deposits, but overweight is not a prerequisite for its occurrence. Slim women increasingly also have pronounced cellulite symptoms. However, there is probably a correlation between the severity of the cellulite and the percentage fat portion in the tissue.

The sex-specific anatomic structure of the skin of the human has a great influence on the development of cellulite. Thus, for example, cellulite can only seldom be observed in men, while, on the other hand, 80%-90% of all women are affected. The structure of the dermis, in particular, has an effect on the skin relief. Thus, the fat chambers in men, when the skin is pressed together, are held back by intersecting connective tissue septa and the clamp-like enclosure connected therewith of the fat cells. On the other hand, in women, the fat chambers separated from one another in a tubular manner, which are enclosed by actinomorphically extending connective tissue septa, bulge up when being pressed together.

In addition, the visible pattern of the cellulite is based on an increase in fat cushions in the subcutis and a reduction in the circulation conditions in the blood and lymph paths. The cause is therefore partly a predisposed weakening of the connective tissue with simultaneous occurrence of enlarged fat cell chambers with stress, sports activity, smoking, pregnancies and female hormones (oestrogen and progesterone) playing a part, in addition to genetic factors.

The conventional treatment methods for cellulite attempt to encourage the blood circulation of the relevant skin parts and to positively influence the connective tissue structure, for example by massage, lymph drainage, diet, sport, magnetic fields or else liposuction (removing fat by suction).

In the literature, the use of phosphodiesterase inhibitors is described to stimulate lipolysis in the fat cells (Cellular Signalling 2006, 18, 401-8). According to Biochem. Pharmacol. 1992, 44, 1307-1315, lipolysis is not basically stimulated by phosphodiesterase inhibitors, as biolysis is influenced by various factors.

Fat metabolism in the fat tissue of the human, in order to reduce the stored lipid quantity, can in principle be regulated by three routes:

Route (i): The differentiation of the precursor cells of the fat cells called preadipocytes to the actual fat cells, called adipocytes, which may store triglycerides, can be inhibited. Expressed more simply, an inhibition of route (i) prevents the build up of cellulite in that the number of fat cells does not increase.

Route (ii): The storage of triglycerides in the adipocytes (also called lipogenesis), can be prevented or inhibited. Expressed more simply, an inhibition of route (ii) prevents the storage of further triglycerides (fats) in the cell and existing fat cells do not store any new fat. Owing to the natural fat metabolism, when route (ii) is inhibited, the fat content in the cell decreases.

Route (iii): An augmented/increased hydrolysis of lipids already stored in the adipocytes—also called lipolysis—is possible by targeted stimulation. Expressed more simply, stimulation of route (iii) increases the breakdown of the fats already present in the cell while an inhibiting, i.e. antagonistic effect with respect to route (iii) on the other hand inhibits or prevents the breakdown of fat.

The differentiation of cells is the changing of the control of the gene activity of a cell so that various protein stores are realised in the cells by means of transcription and protein biosynthesis and the cells differ according to appearance and function. Thus adipocytes only express enzymes, which are necessary for the storing of fats, after differentiation. In their precursor cells of undifferentiated preadipocytes, these enzymes are not expressed or only to a very small extent.

Cosmetic preparations which have the prophylaxis and treatment of cellulite as a goal have already been proposed in the literature.

EP 1 234 572 describes a cosmetic preparation of at least one isoflavone aglycone from the group of genistein, daidzein, glycitein, formononetin, tecyorigenin, irigenin, biochanin A, O-desmethylangolensin, equol, orobol, santal, pratensin and apiosylpuerarin, in particular genistein and/or daidzein, for treating cellulite. The isoflavone aglycone is in this case combined with an algae extract. Genistein is described there as an active ingredient, which inhibits the multiplication of precursor fat cells and in addition the enzyme phosphodiesterase.

A cosmetic preparation of certain biochinones and isoflavonoids, preferably genistein, are described for the prophylaxis of cellulite in DE 10 2004 032 837. It is maintained that the effect of this preparation takes place by means of an improvement in the cell metabolism. It cannot be seen here which mechanism of the cell metabolism is improved. It can also not be inferred there whether the fat tissue is influenced by the cosmetic preparation.

Preparations containing certain isoflavones are also described in DE 100 09 423, the isoflavones being described as materials with an anti-oestrogen effect and used because of this effect. Daidzein, genistein, glycitein, formononetin and others are preferred isoflavones here.

The disadvantage in the prior art is the circumstance that the known preparations only have a limited effectivity in the prophylaxis and treatment of cellulite. In our own extensive investigations, genistein thus exhibited an effect which was strongly dependent on the concentration on the differentiation of fat cells.

Depending on the use concentration of genistein, the differentiation of the fat cells is inhibited or stimulated. The stimulation of the differentiation of precursor cells is not desired in the treatment of cellulite, as the pattern of the cellulite is reinforced thereby. In the production and in vivo use of preparations containing genistein the concentration therefore has to be selected very carefully and the skin penetration by the formulation used taken into account in order to not achieve the antagonistic effect of differentiation stimulation.

Thus, in our own investigations, some of the isoflavones described in the patent literature mentioned above exhibit antagonist effects with regard to the lipolysis of fat cells. The isoflavones santal and formononetin are mentioned as an example which are to be used according to EP 1 234 572 for treating cellulite (called "cellulitis" there), but which in our own investigations exhibited an inhibition of lipolysis.

These isoflavones do not stimulate lipolysis (route iii), but inhibit the breakdown of the triglycerides already stored in the fat cell, in other words with regard to lipolysis, they exhibit an antagonistic effect. Thus, stimulation of lipolysis cannot be concluded on the basis of an inhibition of phosphodiesterase.

It was therefore the object of the invention to disclose active ingredients and corresponding preparations which have a, preferably improved, effectivity with respect to the prophylaxis and treatment of cellulite.

It has surprisingly been found that this object can be achieved by the active anti-cellulite ingredients of formula (I) (pterocarpans) and corresponding preparations, in particular cosmetic, dermatological or pharmaceutical preparations, containing an effective quantity of one or more compounds of formula (I)

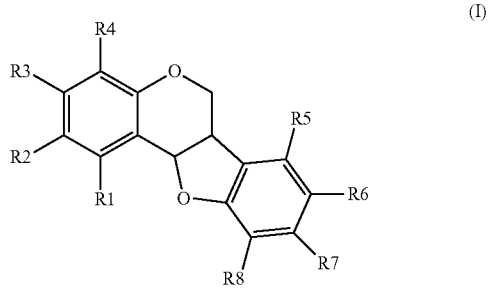

(I)

wherein

R1 to R8, independently of one another may signify hydrogen, hydroxy or $C_1$-$C_4$-alkoxy and in each case two directly adjacent radicals of R1 to R8 may be connected by a methylenedioxy group -O—$CH_2$—O—. Thus, if a radical R1 to R8 together with one of the further radicals R1 to R8, does not form a methylenedioxy group, this radical is hydrogen, hydroxy, methoxy, ethoxy, n-propoxy, iso-propoxy, n-butoxy, iso-butoxy, sec-butoxy or tert-butoxy.

The compounds of formula (I) show a pronounced effect in the treatment of cellulite, recognisably by means of echographic determination of the subcutis layer thickness, in particular to prevent the increased formation of fat stores in the skin and/or cellulite, in that the lipid content in the human subcutaneous fascia fat tissue is reduced. The invention therefore relates to cosmetic preparations containing a corresponding effective quantity of one or more compounds of formula (I), in particular for the topical treatment and prevention of increased formation of fat stores in the skin and/or cellulite.

R1 to R8 preferably signify, independently of one another, hydrogen, hydroxy, methoxy or ethoxy, if two respective adjacent radicals of R1 to R8 do not together form a methylenedioxy group —O—$CH_2$—O—, and wherein, more preferably, R3 is not hydrogen.

Alternatively or in addition, preferably at most three, preferably at most two, of the radicals R1 to R8 simultaneously have the significance hydroxy.

Further preferred according to the invention are compounds of formula (IA)

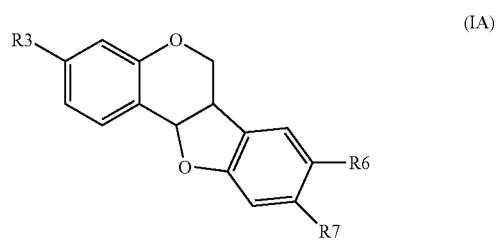

(IA)

wherein the radical R3 signifies hydrogen, hydroxy or methoxy and the radicals R6 and R7 together form a methylenedioxy group or, independently of one another, signify hydrogen, hydroxy or methoxy, and wherein more preferably R3 is hydroxy or methoxy.

Preferred, in particular, are medicarpin, maackiain, pterocarpin, homopterocarpin and 3-methoxypterocarpan (in accordance with the compound of formula (B)). Most preferred for the purposes of the invention is the compound of formula (B).

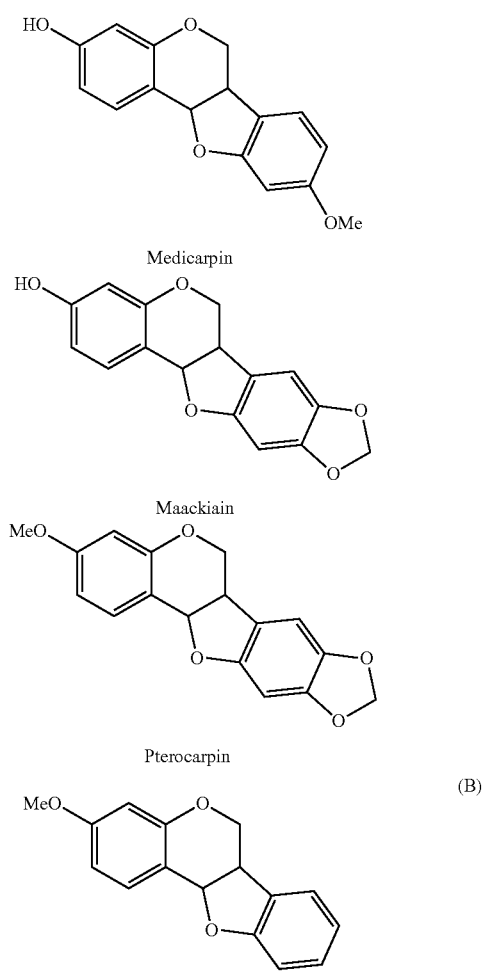

(B)

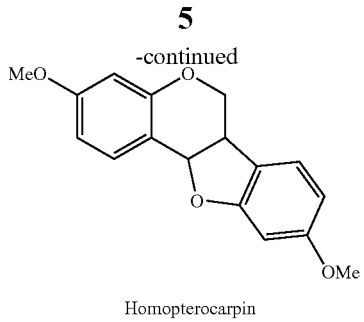

Homopterocarpin

The compounds of formula (I) are structurally to be assigned to the pterocarpans. These are partly so-called phytoalexins, natural compounds which are formed by plants as a result of an infection and are used for defence. The plants which form pterocarpans include, for example, types of the sophora genre. The naturally occurring pterocarpans maackiain and medicarpin have already been extensively investigated as components of plants frequently used in traditional medicine such as *Sophora flavescens, Sophora subprostata* and *Sophora japonica*. Thus, antipyretic, fungicidal, antibacterial and anti-tumour effects are inter alia described in the literature, as are effects against yeasts and snake poison (see the entry in the RÖMPP dictionary and the literature references cited in U.S. Pat. No. 5,721,371).

JP 2002-053421 describes certain pterocarpans, in particular purified Maackiain from roots of Sophora subprostata to inhibit the dendrite growth of melanocytes, i.e. to influence the skin pigmentation.

An inhibition of leukotriene biosynthesis is known from U.S. Pat. No. 4,704,400 for medicarpin and derivatives isolated from *Dalbergia odorifera*.

Various pterocarpans and extracts containing pterocarpans are described in WO 2007/128725 as antagonists of the arylhydrocarbon receptor, which are also used there in cosmetic preparations.

Some pterocarpans are natural materials occurring in legumes with the cis-6a,11a-dihydro-6H-benzofuro[3,2-c][1]benzopyran ring system (pterocarpan). Important representatives are, for example maackiain and pterocarpan. Both enantiomers and also the racemate forms occur in nature. The content of pterocarpans in plants is generally low. It is technically possible to isolate the pterocarpans for use for cosmetic preparations, but it is not economically very sensible because of the low yield.

One synthesis method which is suitable for the production of pterocarpans of formula (I) has been described in U.S. Pat. No. 5,721,371.

An enantiomer separation by means of HPLC of some pterocarpans, inter alia of compound (B) is described in J. Liquid Chromatography & Related Technologies 2005, 28, 823-834.

The compounds of formula (I), in particular those of formula (IA) and (B) can also be produced according to or on the basis of Tetrahedron 1999, 55, 11773-11786.

Furthermore, the compounds of formula (I) can be produced according to or based on Synlett 1994, 1001-1002, J. Chem. Soc., Perkin Trans 1, 1998, 2533-2536 and J. Nat. Prod. 2008, 71, 275-277.

The compounds used according to the invention of formula (I) can also be used in the form of extracts from plants. The extracts to be used according to the invention are preferably obtained from the wood or heartwood of the plants of the genus *Bobgunnia*, preferably from the plant *Bobgunnia madagascariensis*, which belongs to the family Fabaceae, subfamily of the pea family (Faboideae), *Tribus swartzieae*. This plant is also known under the name *Swartzia madagascariensis*, although the genus *Bobgunnia* was already separated off from the genus *Swartzia* in 1997 (Kirkbride et al. Brittonia 1997, pages 1-23). A common designation is also the synonym *Pao rosa*. The plant is a tree or bush which is generally 4-9 m high (up to 20 m) with characteristic white blossom, bushy or with a short trunk of up to 40 an in diameter. The heartwood is purple/black, hard, durable and resistant to termites. The plant is common from the Sahel zone as far as north east Namibia (Hans Dieter Neuwinger: Afrikanische Arzneipflanzen und Jagdgifte, Chemie, Pharmakologie, Toxikologie, Wiss. Vert-Ges. 1998, pages 316-321).

Various applications can be found in traditional medicine depending on the country and tribe. For example, the roots have the reputation of great effectiveness in syphilis and leprosy; cooked roots are used in gastritis; a bark infusion is prescribed in the case of jaundice; the root infusion is drunk in the case of oedemas; the root powder is eaten for diarrhoea (Hans Dieter Neuwinger. Afrikanische Arzneipflanzen und Jagdgifte, Chemie, Phamiakologie, Toxikologie, Wiss. Vert.-Ges. 1998, pages 316-321).

The use of an extract of the husks and seeds as a molluscicide is described and to be attributed to the saponins contained (Suter et al., Acta Tropica 1986, pages 69-83; Borel et al., Helvetica Chimica Acta 1987, pages 570-576).

Georges et al. (Bioresource Technology 2008, pages 2037-2045) describe the use of an extract of leaves of *Swartzia madagascariensis* as an insecticide.

An activity by the extract of root barks of *Bobgunnia madagascariensis* against the intracellular form of *Leishmania major* was described in the Journal of Ethnopharmacology 2007, pages 99-104.

U.S. Pat. No. 5,929,124 describes the use of an extract of the root bark on the basis of antimicrobial activity against candida, *aspergillus, staphylococcus* etc. and the activity is attributed to the diterpenes contained. A use for skin, hair and nails with microbial infections is described, it being possible to apply the extract produced from the root bark or from the diterpenes isolated therefrom topically as well.

An antimicrobial activity of an ethanol extract of the roots of *Bobgunnia madagascariensis* is described by Kone et al. (Journal of Ethnopharmacology 2004, pages 43-49).

Antimicrobial activity has also been established for extract mixtures which contained a methanol extract of the bark of *Swartzia madagascariensis*, by Magassouba et al. (Journal of Ethnopharmacology 2007, pages 44-53).

The heartwood of *Pao rosa* was investigated by Harper et al. (J. Chem. Soc. 1969 1109-1116) with regard to ingredients contained, an identification only being carried out for the ether extract and for the petroleum ether extract. An ethanol extract of the heartwood previously extracted with petroleum and ether was produced but the components contained were not further investigated. In the extracts of the heartwood investigated of *Pao rosa*, various pterocarpans were shown, including homopterocarpin, pterocarpin, 3,9-dimethoxy-pterocarpene and 3,4,9-trimethoxy-pterocarpan.

In WO 2007/128725 A1, pterocarpans and extracts containing pterocarpans are described as aryl hydrocarbon receptor (AhR) antagonists and their use in cosmetic formulations described. Extracts of wood—preferably heartwood—of the *Swartzia* genre as well as, as an example, *Swartzia madagascariensis*, are also mentioned. The extraction takes place here with an extraction agent containing at least one of the following solvents: water, ethyl acetate, an alcohol and/or a ketone selected from the group methanol, ethanol, n-propanol, isopropanol and acetone. A further treatment of the extract is not carried out here, but the latter is used directly as a crude extract.

However, it has been shown in our own investigations that the crude extract of *Pao rosa* heartwood produced according to WO 2007/128725 A1 has phototoxic properties, so the latter is poorly to not at all suited to use in cosmetic preparations. It was also possible to show in our investigations that crude extracts of *Pao rosa* have no further (noteworthy) phototoxic potential after a treatment with activated carbon following the extraction. In the *Pao rosa* heartwood extract according to the invention, apart from pterocarpans, isoflavones, such as, for example, afrormosin were also demonstrated. The isoflavone afrormosin and other methoxylated isoflavones (odoratin, cladastrin and others) exhibit a notable phototoxic potential. In the *Pao rosa* extract produced according to the invention, due to the treatment with activated carbon, the content of afrormosin and other isoflavones is reduced, so the phototoxic potential is reduced.

The phototoxic potential is expressed as a photo-irritation factor (PIF). The PIF of a plant extract containing one or more compounds of formula (I), preferably extracts of (heart) wood of the plants of the genus *Bobgunnia*, preferably *Pao rosa*, is adjusted to a value of less than 5, preferably to a value of less than 2, according to OECD guideline 432 in the version of 13 Apr. 2004. It applies here that with a PIF of less than 2, no phototoxic potential exists while a phototoxic potential exists at a PIF of more than 5. With a PIF of between 2 and 5, there is possibly a phototoxic potential. The extracts according to the invention, preferably from plants of the genus *Bobgunnia*, in particular *Pao rosa* heartwood extracts, after treatment with activated carbon have a PIF of less than 2, i.e. these have no further phototoxic potential according to OECD 432.

According to the invention an extract is produced from wood or heartwood of the plants of the genus *Bobgunnia*, preferably *Pao rosa* heartwood, containing compounds of the formula (I), in particular the compounds maackiain and medicarpin. To be regarded as a dry extract according to the invention, is an extract produced or able to be produced according to the following method after complete removal of the extraction agent. The method according to the invention for producing an extract from *Pao rosa* heartwood comprises the following steps:

(1) providing wood, preferably rasped wood material, from plants of the genus *Bobgunnia*,
(2) adding an extraction agent to the wood provided in step (1), selected from
   A) the group consisting of methanol, ethanol, n-propanol, isopropanol and mixtures of two or more of these extraction agents, or
   B) the group consisting of mixtures of water and one or more of the substances methanol, ethanol, n-propanol and isopropanol,
(3) up to 24 h extraction of the wood to which the extraction agent was added in step (2) to obtain a crude extract, and
(4) treating the crude extract obtained in step (3) with activated carbon to obtain the extract with a photo-irritation factor according to OECD guideline 432 in the version adopted on 13 Apr. 2004 of less than 5, preferably less than 2.

In this case, selected as the rasped wood material are: woodchips, for example planing chips, and/or wood flour, for example sawing flour, and/or wood rasped in another manner.

The ratio of the mass of extraction agent to rasped wood material mass is preferably adjusted such that at least twice the mass of extraction agent based on the rasped wood material mass and preferably not more than 20 times the mass of extraction agent based on the rasped wood material mass is obtained. Particularly preferably 2 to 10 times the mass of extraction agent is used for extraction based on the rasped wood material mass. It was possible to achieve the best results with a 5-fold mass of an ethanol-containing solvent (again based on the rasped wood material mass).

The extraction time to carry out step (3) is at most 24 hours, but may also be shorter. It is preferred for the rasped wood material to be extracted in step b) for at least 1 h, in particular for at least 2 h. The extraction time required to produce an extract for use in cosmetic preparations is preferably at most 24 h and particularly preferably at most 4 h. The required extraction time is selected as a function of the quality of the rasped wood material to be extracted and of the remaining extraction conditions, in particular the extraction temperature.

It is in addition particularly preferred for the extraction in step (3) to be carried out with a backflow of the extraction agent. The extraction temperature is adjusted as a function of the extraction agent used. When using an ethanol-containing solvent, an extraction temperature of 80-100° C. is preferred.

In order to reduce the phototoxicity of the extract, after the extraction in step (4) the crude extract has activated carbon added. The weight ratio of activated carbon to the rasped wood material used in step (2) is preferably selected here such that this is from 1:1 to 1:50, preferably from 1:2 to 1:20 and particularly preferably from 1:5 to 1:10.

Owing to the treatment of the crude extract with activated carbon in step (4), the content of compounds of formula (I), in particular of the compounds maackiain and medicarpin, increases.

On the other hand, the content of the isoflavone afromosin, which is known for a high phototoxic potential, is reduced.

The extract should be free of extraction agent for use in cosmetic preparations. The extraction agent should be removed completely as far as possible by a suitable method (for example distillation, drying, freeze drying).

The preparations according to the invention, containing one or more compounds of formula (I) influence cellulite with regard to the stored lipid quantity, in that the lipid content in human subcutaneous fascia fat tissue is reduced.

In addition, the preparations according to the invention have a positive effect on skin irritations, which may accompany cellulite.

Thus cellulite is prevented, treated or reduced by a preparation containing one or more compounds of formula (I) by influencing the above-described routes (i) and (ii). The lipolysis (route (iii)) is not influenced by the compounds of formula (I). In contrast to the isolflavones mentioned in the prior art cited above, the compounds do not influence route (iii) antagonistically.

It is obvious that instead of preparations containing pure materials of formula (I), preparations containing an extract of *Pao rosa* heartwood can also be used according to the invention. Preparations of this type also influence cellulite by influencing the routes (i) and (ii). The extract of *Pao rosa* heartwood is distinguished here by a high total content of pterocarpans, in particular maackiain and medicarpin, from 5% by weight to 25% by weight, based on the dry extract.

A cosmetic, preferably topical preparation according to the invention preferably contains one or more compounds of formula (I) without taking into account possible counterions in a total quantity of 0.001-1.0% by weight, preferably 0.005-0.5% by weight and particularly preferably 0.01-0.15% by weight and most preferably 0.02-0.10% by weight, in each case based on the total weight of the preparation.

Alternatively, a preparation according to the invention is preferred containing a *Pao rosa* heartwood dry extract according to the invention in the range of 0.001-5% by weight, preferably in a concentration of 0.01-0.50% by weight, more preferably in a concentration of 0.02-0.20% by weight, in each case based on the total weight of the preparation.

The compounds of formula (I), optionally in the form of an extract according to the invention, can easily be incorporated in these concentrations in common cosmetic or dermatological formulations such as pump sprays, aerosol sprays, creams, ointments, tinctures, lotions and the like. In this case, it is also possible and in many cases advantageous to combine the compounds of formula (I) with further active ingredients.

The invention consequently relates to (improved) cosmetic preparations containing:
(a) One or more compounds of formula (I), optionally in the form of a plant extract, preferably of the genre *Bobgunnia*, and
(b) one or more lipolysis stimulants.

Lipolysis stimulants are active ingredients which stimulate lipolysis (route (iii)) and are preferably selected
from the group (b-i) of inhibitors of phosphodiesterase and/or
the group (b-ii) of agonists of beta-adrenergic receptors.

Expediently, the lipolysis stimulant is present in a quantity sufficient to stimulate lipolysis.

An advantageous preparation according to the invention additionally contains anti-cellulite active ingredients from the group of xanthines, preferably selected from the group of optionally substituted 3,7- or 3,9-dihydro-1H-purin-2,6-diones of the formula (Xa):

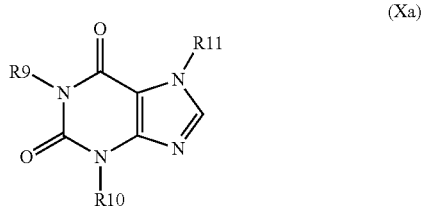

wherein R9, R10 and R11, independently of one another, signify hydrogen or methyl.

The xanthines, in particular those of formula (Xa), may preferably be used as pure materials or else in the form of plant extracts.

The methyl xanthines are preferably caffeine ($R9=R10=R11=CH_3$), theobromine ($R9=H$, $R10=R11=CH_3$) and theophylline ($R9=R10=CH_3$, $R11=H$); the most preferred xanthine in the sense of the present invention is caffeine. Also preferred is the theophylline derivative aminophylline.

Particularly preferably, a cosmetic, preferably topical preparation according to the invention contains one or more compounds of formula (Xa), in turn preferred here caffeine, preferably in a total quantity of 0.005-10% by weight, preferably 0.05-5% by weight, particularly preferably 0.5-2.5% by weight, in each case based on the total weight of the preparation, counterions of the compounds of formula (Xa) not being included.

Preferred weight ratios of the total quantity of the compound of formula (I) to the total quantity of xanthines of formula (Xa), caffeine being preferred here, in the preparations according to the invention are preferably from 1:1 to 1:500, more preferably from 1:5 to 1:125, also without taking into account possible counterions.

Also preferred preparations contain combinations of the compound of formula (I) with an agonist of beta-adrenergic receptors of adipocytes. Preferred agonists of beta-adrenergic receptors are β-phenylethylamines of formula (PhEA):

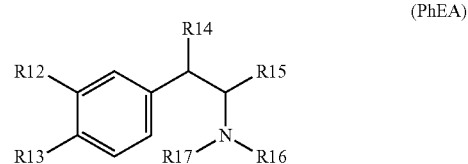

wherein
R12 and R13, independently of one another, signify hydrogen, hydroxy or methoxy,
R14 signifies hydrogen, hydroxy or methyl,
R15 signifies hydrogen or methyl
R16 and R17, independently of one another, signify hydrogen or $C_1$-$C_4$-alkyl.

The β-phenylethylamines of formula (PhEA) can preferably be used as pure substances, in the form of their respective hydrochlorides or in the form of plant extracts.

Preferred agonists of beta-adrenergic receptors are adrenaline, noradrenaline, metanephrine, macromerine, normacromerine, hordenine, N-methyltyramine, dopamine, octopamine, tyramine, 2-phenylethylamine, phenylethanolamine, epinine (N-methyldopamine), synephrine, ephedrine, pseudoephedrine, norephedrine and isoprenaline.

Some of these compounds had already been investigated in the literature for their activity with regard to the beta-3-adrenergic receptor in human fat cells and mammals (Naunyn-Schmiedeberg's Archives of Pharmacology 1999, 359, 310-321).

Compounds of formula (PhEA) in which R17=H and R16 signifies hydrogen or $C_1$-$C_4$-alkyl, preferably hydrogen, methyl or iso-propyl are preferred. Further preferred are compounds of formula (PhEA), in which additionally R15=H.

In a further preferred configuration, the agonists of beta-adrenergic receptors are those compounds in which R12 and R17=H.

Particularly preferred agonists of beta-adrenergic receptors correspond to the formula (PhEA-i), and in turn preferred here are tyramine, N-methyltyramine, octopamine and synephrine.

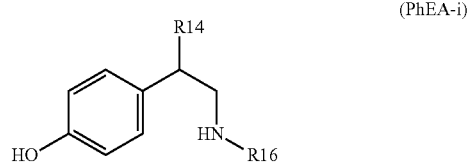

wherein the radicals R14 and R16 have the aforementioned (preferred) significance.

The most preferred agonist of a beta-adrenergic receptor is synephrine (R14=OH, $R16=CH_3$ in formula (PhEA-i)), preferably racemic or enantiomer-pure, in this case in turn preferred is the (−)-form.

Likewise particularly preferred are synephrine-containing extracts, such as, for example, orange blossom extract.

A cosmetic, preferably topical preparation according to the invention particularly preferably contains an agonist of a beta-adrenergic receptor, in this case preferably synephrine, preferably in a total quantity of 0.0001-0.10% by weight, preferably 0.001-0.05% by weight, more preferably 0.002-0.02% by weight, in each case based on the total weight of the preparation, the counterion of the agonist not being included in the case of salts.

The weight ratios of the total quantity of the compound of formula (I) to the total quantity of agonists of a beta-adrenergic receptor, in particular to synephrine in preparations according to the invention are preferably selected from 100:1 to 1:5, more preferably from 50:1 to 1:1, most preferably from 25:1 to 2:1.

As the occurrence of cellulite, in addition to an increased storage of fat in the fat tissue, is generally also accompanied by a breakdown of the connective tissue, preferred cosmetic preparations according to the invention containing one or more compounds of formula (I) may also contain active ingredients which prevent a breakdown of the connective tissue. Active ingredients are advantageous here which inhibit matrix-metallo-proteinases (MMPs). These enzymes are in a position to break down macromolecules of the extracellular matrix (ECM)/of the connective tissue, also including the collagens, proteolytically. In particular the matrix-metallo-proteinase-1 (MMP-1), matrix-metallo-proteinase-2 (MMP-2) and matrix-metallo-proteinase-9 (MMP-9) are responsible for the breakdown of the connective tissue of the skin. An inhibition of MMPs is possible, for example, by the addition of ursolic acid, retinyl palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1 (2H)-benzopyran. An addition of peptides, which inhibit MMPs, to preparations according to the invention, is also advantageous to inhibit MMPs. Proteins or glycoproteins from soya and hydrolysed proteins from rice, pea or lupine also inhibit MMPs and are therefore a suitable addition. A combination with a plant extract, which inhibits MMPs is also advantageous. To be mentioned here by way of example is an extract from shitake mushrooms. The combination with extracts from the leaves of the Rosaceae family, sub-family Rosoideae, is also advantageous. Quite particularly advantageous is the use of blackberry extract, in particular as described in WO 2005/123101 A1.

MMP inhibitors to be preferably used in combination in the scope of the present invention are retinyl palmitate, propyl gallate, precocenes, 6-hydroxy-7-methoxy-2,2-dimethyl-1 (2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsulfonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic add, soya isoflavones and soya proteins), sage extracts, MDI (company Atrium; INCI: glycosaminoglycans), fermiskin (company Silab/Mawi; INCI: water and *lentinus edodes* extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and numerous further plant extracts, which are listed in WO 02/069992 (see table 1-12 there).

In order to counteract the breakdown of the connective tissue, the combination of active ingredients, which encourage the formation of collagen in the tissue is furthermore advantageous in preferred cosmetic preparations according to the invention containing one or more compounds of formula (I). Individual substances frequently used to increase collagen synthesis are, for example, active ingredients such as ascorbic acid and their derivatives, retinol and derivatives of retinol or plant extracts such as, for example, extracts of aloe and centella types. Moreover peptidic materials and their derivatives, such as, for example, carnitine, carnosine, creatine, matrikine peptides (e.g. lysyl-threonyl-threonyl-lysyl-serine) and further peptidic structures such as palmitoylated pentapeptides (for example matrixyl/company Sederma) or the oligopeptide with the trade name Vincipeptide (company Vincience/France) are also included in the frequently used active ingredients increasing collagen synthesis. Furthermore, compounds such as Asiatic acid, madecassic acid, madecassoside, asiaticoside, extracts of Centella asiatica, niacinamide, astaxanthine, glucans, for example from yeast and oats, soya extracts and soya isoflavones such as genistein and daidzein, rutin, chrysin, morin, betel nut alkaloids, forskolin, betulinic acid, extracts of *plantago* genres. TGF-beta, extracts from *Ginkgo biloba*, glutamine and glycolic acid are also used as collagen synthesis stimulators. Particularly preferred here is the addition of a combination of aloe vera extract, raspberry extract and magnesium ascorbyl phosphate.

Further preferred preparations according to the invention containing one or more compounds of formula (I) further comprise additionally (i) coenzyme A to promote the transport of free fatty acids in the mitochondria and/or (i) L-carnitine to encourage beta-oxidation.

Substances and auxiliaries which may additionally contain a preparation according to the invention containing one or more compounds of formula (I) are, for example:

preservatives, preferably the abrasives, anti-acne agents and agents for sebum reduction mentioned in US 2006/0089413, preferably the agents mentioned in WO 2008/046791 against skin ageing, preferably the antibacterial agents, anti-cellulitis agents, anti-dandruff agents mentioned in WO 2005/123101, preferably the anti-inflammatory agents, irritation-preventing agents, anti-irritants (anti-inflammatory, irritation-inhibiting and irritation-preventing agents) mentioned in WO 2008/046795, preferably the antimicrobial agents mentioned in WO 2007/042472 and US 2006/0089413, preferably the antioxidants mentioned in WO 2005/123101, preferably the adstringents, antiseptic agents, antistatics, binders, buffers, carrier materials mentioned in WO 2005/123101, preferably the chelating agents mentioned in WO 2005/123101, preferably the cell stimulants, cleaning agents, care agents, depilatory agents, surfactant substances, deodorising agents and antiperspirants mentioned in WO 2005/123101, preferably the softeners, emulsifiers mentioned in WO 2005/123101, preferably the enzymes, essential oils mentioned in WO 2005/123101, preferably the insect repellents mentioned in US 2008/0070825, preferably the fibres, film formers, fixing agents, foam forming agents, foam stabilisers, substances for preventing foaming, foam boosters, fungicides, gelling agents and gel-forming agents mentioned in WO 2005/123101, preferably the hair care agents, hair shaping agents, hair smoothing agents, moisture regulators (moisture-dispensing, moisturising and/or moisture-containing substances) mentioned in WO 2005/123101, preferably the osmolytes mentioned in WO 2005/123101, preferably the compatible solutes mentioned in WO 2005/123101, preferably the bleaching agents, strengthening agents, stain-removing agents, optically brightening agents, impregnating agents, dirt-repellent agents, friction-reducing agents, lubricating agents, moisture creams, ointments, opacifying agents, plasticizing agents, covering agents, polishes, brighteners, polymers mentioned in WO 01/76572 and WO 02/15686, preferably the powders, proteins and protein hydrolysates mentioned in WO 2008/046676, preferably the lipid regulating agents, exfoliating agents, skin-calming agents, skin cleaning agents, skin care agents, skin repair agents, preferably containing cholesterol and/or fatty acids and/or ceramides and/or pseudoceramides mentioned in WO 2005/123101 and WO 2008/046676, in this case preferably the skin brightening agents mentioned in WO 2006/053912, preferably the skin protecting agents, skin softening agents, skin cooling agents mentioned in WO 2007/110415, preferably the skin warming agents mentioned in WO 2005/123101, preferably the stabilisers, UV-absorbing agents and UV filters mentioned in WO 2005/123101, preferably the benzylidene-beta-dicarbonyl compounds mentioned in WO 2005/123101, preferably the alpha-benzoyl cinnamic acid nitriles mentioned in WO 2005/107692, preferably the AhR-receptor antagonists mentioned in WO 2006/015954, preferably the detergents, fabric softeners, suspending agents, skin tanning agents mentioned in WO 2007/060256, preferably the thickeners, vitamins mentioned in WO 2006/045760, preferably the oils, waxes and fats mentioned in WO 2005/123101, preferably the phospholipids mentioned in WO 2005/123101, preferably the fatty acids (saturated fatty acids, singly or multiply unsaturated fatty acids, α-hydroxy acids, polyhydroxy fatty acids) mentioned in WO 2005/123101, preferably the liquefiers, dyes and colour-protecting agents and pigments mentioned in WO 2005/123101, preferably the anti-corrosives, flavours and flavour additives and perfumes mentioned in WO 2005/123101, preferably the alcohols and polyols listed in S. Arctander, Perfume and Flavor Chemicals, self-published, Montclair, N.J., 1969 and Surburg, Panten, Common Fragrance and Flavor Materials, 5$^{th}$ Edition, Wiley-VCH, Weinheim 2006, in particular the alcohols and polyols explicitly mentioned in US 2008/0070825, preferably the surfactants mentioned in WO 2005/123101, preferably the animal extracts, yeast extracts, extracts of algae or microalgae, electrolytes, liquefiers, organic solvents mentioned in WO 2005/123101, preferably those mentioned in WO 2005/123101, or silicones and silicone derivatives, preferably those mentioned in WO 2008/046676.

Also advantageous are preparations according to the invention which are administered orally, for example in the form of tablets (for example film tablets), coated tablets, capsules (for example gelatin capsules), granulates, juices, solutions emulsions, micro emulsions, sprays or products which can be consumed orally in another form, or in the form of food, which, because of the compound(s) contained therein of formula (I) bring about "beauty from inside".

Preferred cosmetics carrier materials, which may be a component of a preparation according to the invention are solid or liquid at 25° C. and 1013 mbar (including highly viscous substances).

Preferred liquid carrier substances, which may be a component of a preparation according to the invention are selected from the group consisting of glycerol, 1,2-propylene glycol, 1,2-butylene glycol, 1,3-butylene glycol, 1,2-pentandiol, 1,2-hexandiol, 1,2-octiandiol, 1,2-decandiol, ethanol, water and mixtures of two or more of said liquid carrier materials with water. Optionally, these preparations according to the invention may be produced using preservatives, solubilizers or antioxidants.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

Furthermore, the preparations according to the invention may be present in encapsulated form, these preferably being encapsulated with a solid covering material, which is preferably selected from starches, degraded or chemically or physically modified starches (in particular dextrins and maltodexterins), gelatins, gum arabic, agar-agar, ghatti gum, gellan gum, modified and non-modified celluloses, pullulan, curdlan, carrageenans, alginic acid, alginates, pectin, inulin, xanthan gum and mixtures of two or more of said substances.

The solid covering material is preferably selected from gelatin (preferred are pork, beef, chicken and/or fish gelatins and mixtures thereof, preferably comprising at least one gelatin with a bloom value of greater than or equal to 200, preferably with a bloom value of greater than or equal to 240), maltodextrin (preferably obtained from maize, wheat, tapioca or potato, preferred maltodextrins have a DE value of 10-20), modified cellulose (for example cellulose ether), alginates (for example Na-alginate), carrageenan (beta-, iota-, lambda- and/or kappa carrageenan), gum arabic, curdlan and/or agar-agar. Gelatin is preferably used, in particular, because of its good availability in different bloom values. Particularly preferred, especially for oral use are seamless gelatin or alginate capsules, the coveting of which dissolves very rapidly in the mouth or bursts when chewing. Production may take place, for example, as described in EP 0 389 700, U.S. Pat. No. 4,251,195, U.S. Pat. No. 6,214,376, WO 03/055587 or WO 2004/050069.

Important areas of application for the preparations according to the invention are cosmetic, in particular dermatological preparations, which are composed as conventional (apart from the compound(s) of formula (I)) and are used for cosmetic, in particular dermatological light protection, for treatment, care and cleaning of the skin and/or hair or as a make-up product in decorative cosmetics. Accordingly, preparations of this type, depending on their structure, can be used, for example, as day protection cream, day or night cream, eye cream, sun protection or after-sun lotion, nourishing cream, a care mask, gel pads, facial tonic, moist care and cleaning tissues, cleaning milk, cleaning soap, foam or shower bath, deodorant, antiperspirant, hair shampoo, hair care agent, hair conditioner, hair colorant, hair styling agent and in this case preferably be present as an emulsion, lotion, milk, fluid, cream, hydro dispersion gel, balm, spray, alcoholic or aqueous/alcoholic solution, foam, powder, liquid soap, piece of soap, shampoo, roll-on, stick or make-up. In hair treatment agents, the use is preferably directed at the base of the hair or the scalp.

The one or more further substances with a physiological cooling effect, which can be used as a component in a mixture according to the invention, are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (I-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthytglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005/049553, methanecarboxylic add-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric add-N-methylamide [WS23]), isopulegol or its esters (I—(-)-isopulegol, I—(-)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840).

The or the plurality of further substances with a physiological cooling effect, which can be used as a component of a mixture according to the invention, are in particular preferably substances, which at least substantially cause a physiological cooling effect. Such preferred substances are: menthylethers (for example (I-menthoxy)-1,2-propandiol, (I-menthoxy)-2-methyl-1,2-propandiol), polar menthylesters (for example menthyllacetates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate), the semi-esters of menthols with a dicarboxylic acid or derivates thereof (for example mono-menthylsuccinate, mono-menthylglutarate, mono-menthylmalonate, O-menthyl succinic acid ester-N,N-(dimethyl) amide, O-menthyl succinic acid esteramide), not according to the invention, menthane carboxylic acid amides (for example menthane carboxylic acid-N-ethylamide [WS3], $N^\alpha$-(menthanecarbonyl)glycinethylester [WS5], menthane carboxylic acid-N-(4-cyanophenyl)amide, menthane carboxylic acid-N-(alkoxyalkyl)amides), menthane derivatives (for example L-menthone glycerol ketal), 2,3-dimethyl-2-(2-propyl)-butyric acid derivates (for example 2,3-dimethyl-2-(2-propyl)-butyric acid-N-methylamide), pyrrolidone derivatives of cycloalkyldione derivatives (for example 3-methyl-2(1-pyrrolidinyl)-2-cyclopentene-1-one) or tetrahydropyrimidine-2-ones (for example iciline or related compounds, which are described in WO 2004/026840).

Components which cause a hot, sharp, tingly or prickly feeling on the skin or on the mucous membranes, in particular flavours with a heat-producing effect and/or sharp tasting compounds (sharp substances) which may, apart from one or more compounds of formula (I), be a component of a preparation according to the invention, are mentioned in WO 2005/123101.

For use in the conventional manner for cosmetics and skin ointments, the compounds of formula (I) are applied to the skin and/or the hair in an adequate quantity. Particular advantages are offered here by cosmetic dermatological preparations which contain one or more compounds of formula (I) and additionally act as a sun protection means. Advantageously, these preparations contain at least one UVA filter and/or at lease one UVB filter and/or at least one inorganic pigment. The preparations may be present here in various forms such as are conventionally used for sun protection preparations, for example. Thus, they make for example, from a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

Preparations according to the invention in the cosmetics and skin ointment area, which contain one or more compounds of formula (I), are particularly advantageously combined with substances which absorb or reflect UV radiation, especially for cosmetic or skin-protecting purposes (in other words not for oral hygiene purposes), the total quantity of the filter substances being from 0.01% by weight to 40% by weight, preferably 0.1% to 10% by weight, in particular 1.0 to 5.0% by weight based on the total weight of the preparations, in order to provide cosmetic preparations, which protect the hair or the skin from ultraviolet radiation. These preparations advantageously contain at least one UVA filter and/or at least one UVB filter and/or at least one inorganic pigment, so a light protection factor of at least >2 (preferably >5) is achieved. These preparations according to the invention may in this case be present in various forms such as, for example, are conventionally used for sun protection preparations. They may thus be, for example, a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

Advantageous UV filters and inorganic light protection pigments are mentioned in WO 2005/123101. UV absorbers particularly suitable for combination are also mentioned in WO 2005/123101.

Advantageous inorganic light protection pigments are finely dispersed metal oxides and metal salts which are also mentioned in WO 2005/123101. The total quantity of inorganic pigments, in particular hydrophobic inorganic micropigments in the finished cosmetic preparations is advantageously from 0.1 to 30% by weight, preferably 0.5 to 10.0, based on the total weight of the preparations.

A combination with (metal)-chelating agents may also be advantageous in some preparations. (Metal)-chelating agents to be preferably used are the compounds mentioned in WO 2005/123101.

Cosmetic preparations preferred according to the invention can also contain anti-inflammatory and/or redness and/or itch ameliorating active ingredients. The compounds mentioned in WO 2005/123101 are advantageously used as anti-inflammatory or redness and/or itch ameliorating active ingredients.

The quantity of anti-irritants (one or more compounds) in the preparations according to the invention are preferably 0.0001 to 20% by weight, particularly preferably 0.0001-10% by weight, in particular 0.001-5% by weight based on the total weight of the preparation.

The one or more compounds of formula (I) may advantageously be used, in particular, in cosmetic and dermatological preparations in combination with insect repellents such as, for example, DEET, IR 3225, dragorepel (Symrise GmbH & Co. KG).

The one or more compounds of formula (I) can advantageously be used in particular in cosmetic and dermatological preparations in combination with hair care agents and anti-dandruff active ingredients (for example climbazole, ketoconazole, piroctone oleamine, zinc-pyrithione).

The compounds of formula (I) can also advantageously be used in numerous cases in combination with one or more preservatives in preparations according to the invention. The preservatives mentioned in WO 2005/123101 are preferably selected here.

Preparations according to the invention, apart from one or more compounds of formula (I), may also contain plant extracts which can be used for cosmetic purposes. The plant extracts are preferably selected from the table of listed substances beginning on page 44 of the third edition of the handbook on the contents declaration of cosmetic agents, published by the Industrieverband Körperpflegemittel and Waschmittel e.V. (IKW), Frankfurt. The extracts mentioned in WO 2005/123101 are also particularly advantageous.

Cosmetic preparations containing one or more compounds of formula (I) may, in particular if crystalline or microcrystalline solid bodies such as, for example, inorganic micropigments are to be incorporated in the preparations, according to the invention also contain anionic, cationic, non-ionic and/or amphoteric surfactants mentioned in WO 2005/123101.

The surface-active substance may be present in a concentration between 1 and 98% by weight in the preparations according to the invention, based on the total weight of the preparations.

The oil phase of preparations according to the invention, which contain one or more compounds of formula (I) may advantageously be selected from the substance groups mentioned in WO 2005/123101.

The invention will be further described in more detail below with the aid of examples. The examples are used to clarify the invention, without limiting the area of protection of the claims. If not otherwise stated, all the details relate to the weight.

The compounds of formula (I) used in the assays described below were either synthesised in pure form (compound (B)) or isolated from *Pao rosa* heartwood extract (containing maackiain and medicarpin).

EXAMPLE 1

Production of 3-methoxypterocarpan compound (B)

Example 1.1

1-(2,4-dimethoxyphenyl)-2-(2'-methoxyphenyl)-1-ethanone

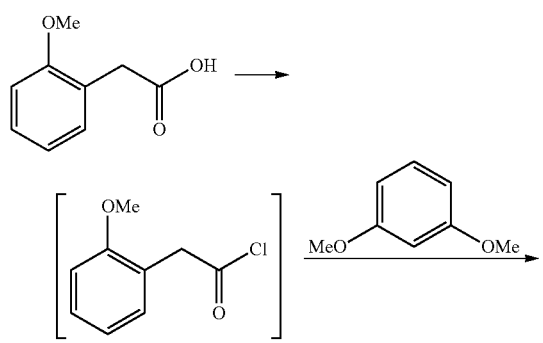

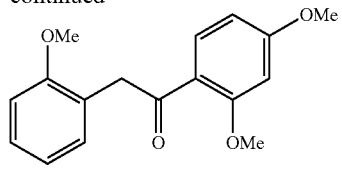

66 g (0.55 mol) thionyl chloride are prepared under $N_2$-atmosphere and with the addition of 0.4 g urea, 66 g (0.40 mol) 2-methoxyphenyl acetic acid are then added while stirring, in a plurality of portions within 30 min. After 2 h backflow 90 g dichloromethane are added and this solution is metered into a mixture of 69 g (0.50 mol) resorcindimethylether and 67 g (0.50 mol) $AlCl_3$ in 300 g dichloromethane within 1 h at RT (room temperature; about 20° C.). Stirring is continued for 2 h and hydrolysis takes place in 500 g ice water. Rinsing takes place to neutral with water and Na-bicarbonate, the dichloromethane is distilled off and the residue distilled from toluene. Yield: 177 g (60% d.Th.)

Example 1.2

1-(2,4-dimethoxyphenyl)-2-(2'-methoxyphenyl)-2-hydroxymethylene-1-ethanone

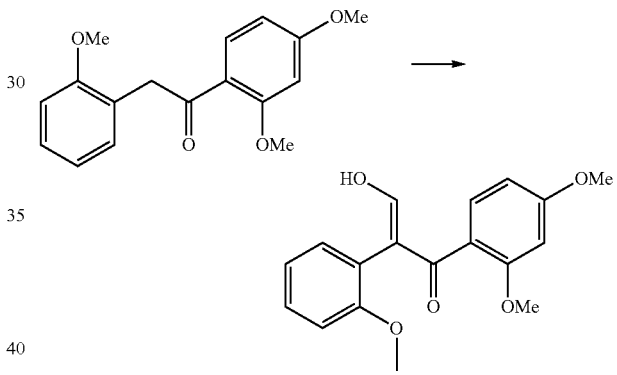

4.2 g (78 mmol) Na-methylate are prepared in 300 g methyl-tert.-butylether (MTBE) under $N_2$-atmosphere and with stirring. At 5° C., a solution of 177 g (0.62 mol) of the product from example 1.1 and 50 g (0.83 mol) methylformiate in 180 g tetrahydrofurane are metered within 30 min. 30 g (0.56 mol) Na-methylate are then added and stirred for 16 h at RT. After hydrolysis with 800 g water with cooling and a further addition of 100 g MTBE, the phases are separated. The aqueous phase is adjusted to pH 5-6 with 10% hydrochloric acid and extracted with 400 g MTBE. After concentration 150 g product are present. Yield: 150 g (79% d. Th.)

Example 1.3

2'-hydroxy-7-methoxy-isoflavone

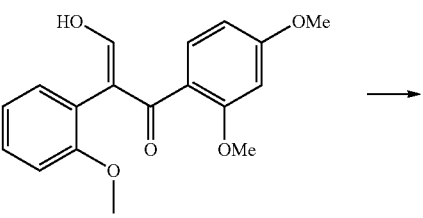

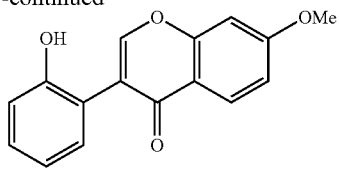

24 g (76 mmol) product from example 1.2 are prepared in 100 g dichloromethane with stirring and an $N_2$-atmosphere and within 300 g (0.3 mol) of a 1M solution of bortrichloride in dichloromethane are metered. Stirring is continued for 18 h at 30-40° C., and hydrolysis takes place with 300 g water with cooling. After phase separation, the organic phase is rinsed to neutral and after removal of the solvent, the residue is recrystallised from ethanol. Yield: 8 g (40% d. Th.)

Example 1.4

3-methyoxypterocarpan (compound (B))

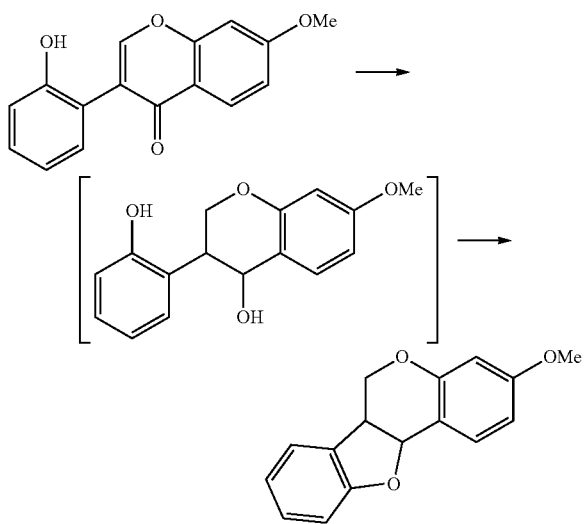

45 g (0.17 mol) of the product from example 1.3 are dissolved in 1000 g ethanol with stirring, 64 g (0.1 mol) Na-borhydride are added in portions at RT and stirred for 4 h. The solvent is then removed at a sump temperature of 50° C. under a vacuum and the remaining residue has 500 g MTBE and 500 g water added, is adjusted to neutral with 10% hydrochloric acid and then phases are separated. 1.2 g bortrifluoride etherate (48%/5 mmol) are added to this solution at 0° C., stirred for 2 h at this temperature and a further 3 h at 40° C. It is rinsed to neutral with water and Na-bicarbonate, the organic phase is concentrated to about 150 g and cooled RT, after which the product is precipitated as a white crystallisate. After drying and recrystallisation, 26 g (60% d. Th.) of the product of formula (B) are present.

EXAMPLE 2

Production of *Pao rosa* Heartwood Extract

According to the invention, a dry extract is produced from *Pao rosa* heartwood containing compounds of formula (I), in particular the compounds maackiain and medicarpin.

According to the invention an extract is produced as the dry extract according to the following method after complete removal of the extraction agent. The method for producing a dry extract from *Pao rosa* heartwood comprises the following steps:

(a) adding to rasped wood material produced from deposited *Pao rosa* heartwood, 5 times the mass of extraction agent (a mixture of water and ethanol with a fraction of ethanol of 30%), (b) extracting the rasped wood material with the extraction agent for a period of 2-4 h, an extraction temperature of 80-100° C. being maintained.

(c) treating the crude extract with activated carbon, the weight ratio of activated carbon to rasped wood material used in item a) being 10:1.

Characterisation of the extract takes place by HPLC fingerprint analysis and quantitative determination of the content of the isoflavonoids and pterocarpans: column: YMC ODS-AQ, 5 μm, 150×3 mm with precolumn, temperature: 40° C., flow: 0.6 ml/min, acetonitrile/water with 0.1% formic acid gradient, injection volume, 5 μl, detection wavelength: 232 nm.

Figure 1:
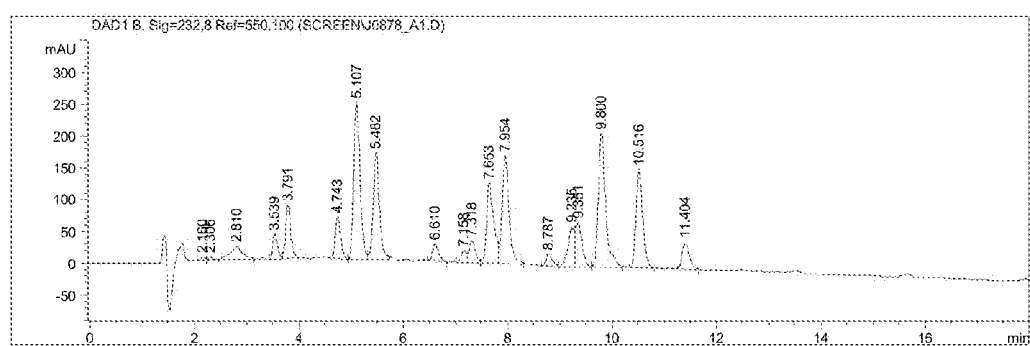
FIG. 1 shows the HPLC chromatogram obtained for a *Pao rosa* crude extract before treatment with activated carbon.
Figure 2:
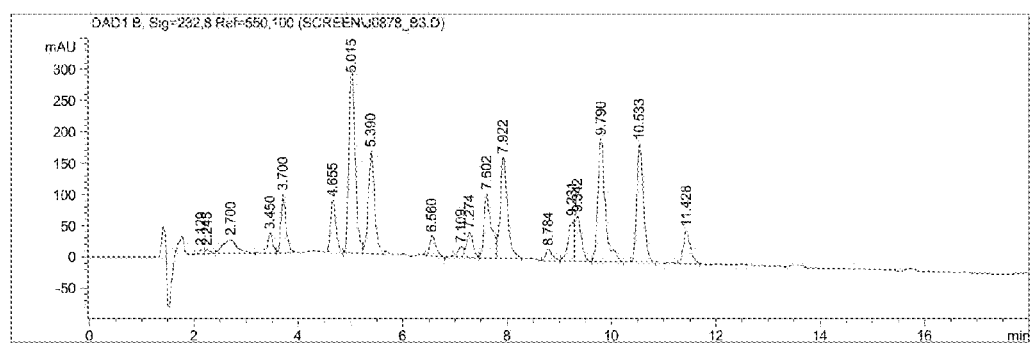
FIG. 2 shows the HPLC chromatogram obtained for a *Pao rosa* dry extract after the treatment with activated carbon.

Because of the treatment of the crude extract with activated carbon in step c), the content of compounds of formula (I), in particular the compounds maackiain and medicarpin, increases. On the other hand, the content of the isoflavone afrormosin, which is known for a high phototoxic potential, is reduced.

TABLE 2.1

Example of the content of the pterocarpans maackiain and medicarpin and the isoflavone afrormosin in a Pao rosa heartwood extract before and after the treatment with activated carbon, the content is given based on the dry substance content of the corresponding extract.

| Retention time | Substance | HPLC Content Extraction up to & incl. b) | HPLC Content Extraction up to & incl. c) |
|---|---|---|---|
| 5.3 min | Di-hydroxy-dimethoxy isoflavone MG: 314 odoratin | 3.8% | 4.5% |
| 5.7 min | Di-hydroxy-trimethoxy isoflavone MG: 344 | 4.7% | 4.8% |
| 8.0 min | Isoflavone MG: 328 | 3.9% | 3.3% |
| 8.4 min | 2',7-dihydroxy-4',6-dimethoxyisoflavone (MG: 314) | 5.8% | 5.8% |
| 10.3 min | Afrormosin MG: 298 | 8.4% | 7.0% |
| 11.1 min | Maackiain MG: 284 | 9.7% | 11.8% |
| 12.0 min | Medicarpin MG: 270 | 2.1% | 2.5% |

The extract should be free of extraction agent for use in cosmetic preparations. The extraction agent should be removed completely as far as possible by a suitable method (for example distillation, drying, freeze drying).

EXAMPLE 3

Lipogenesis Assay (In Vitro)

3T3-L1-cells (mouse embryonal fibroblast-like adipocyte cell line) are seeded in a 48-well plate with collagen I-coating in a concentration of $3 \times 10^4$ cells/well. After 72 h cultivation at 37° C. and 5% $CO_2$ in DMEM (Dulbecco's Modified Eagle Medium), enriched with 10% calf serum, various concentrations of the test substances in DMEM, enriched with 10% foetal calf serum and to which are added 1 µg/ml insulin, 0.25 µM dexamethasone and 0.5 mM IBMX (3-isobutyl-1-methylxanthine), are added and incubated for a further 48 h. A media change takes place, in that DMEM, enriched with 10% foetal calf serum and with 1 µg/ml insulin added, are applied. After renewed cultivation for 48 h, a further media change takes place, in which DMEM, enriched with 10% foetal calf serum, is applied.

After a further incubation for 72 h, the intracellularly stored lipids are quantified as a measure for the differentiation of the cells by measuring the fluorescence after dyeing of the lipids with the fluorescent dye Nile Red.

The inhibition of the adipogenesis in the presence of the test substances is calculated according to the following equation:

$$\text{Inhibition of the adipogenesis [\%]} = 100 - \left( \frac{RFU \text{ test substance} - RFU \text{ control without cells}}{RFU \text{ control} - RFU \text{ control without cells}} \times 100 \right)$$

wherein

RFU test substance=relative fluorescent units of the wells with test substance and with cells RFU control=relative fluorescent units of the wells without test substance, but with cells RFU control without cells=relative fluorescent units of the wells without test substance and without cells The $IC_{50}$ is calculated from the adipogenesis inhibition (%) in a series of dilutions of tested samples. This is the concentration at which the adipogenesis is 50% inhibited.

TABLE 3.1 adipogenesis inhibition of the individual substances
(mean values of at least 2 independent tests)

| Test Substance | $IC_{50}$ (ppm) |
|---|---|
| 3-methoxypterocarpan | 50.9 |
| Medicarpin | 54.0 |
| Maackiain | 25.5 |
| Pao rosa heartwood extract | 4.7 |

EXAMPLE 4

Lipogenesis Assay (In Vitro)

Lipogenesis is taken to mean the storing of triglycerides in adipocytes. The inhibition of this storage can take place by means of the inhibition of the activity of extracellular lipoprotein lipase (LPL) in that the hydrolysis of extracellular triglycerides and therefore the absorption of free fatty acids by adipocytes is reduced. As a preliminary test, the inhibition of pancreatic lipase (PL) is investigated.

PL (Sigma-Aldrich), in the presence of test substances in different use concentrations has methylumbelliferyl oleate (MUF oleate) added as a substrate. Fluorescent methylumelliferon (MUF), is produced by hydrolysis of the MUF oleate by PL and is quantified. The inhibition of the hydrolysis of the MUF oleate is a measure of the inhibition of activity of the PL.

$$\text{Inhibition of the PL [\%]} = 100 - \left( \frac{MUF \text{ test substance} - MUF \text{ control without } PL}{MUF \text{ control} - MUF \text{ control without } PL} \times 100 \right)$$

wherein

MUF test substance=MUF–concentration of the wells with test substance and with PL MUF control=MUF–concentration of the wells without test substance, but with PL MUF control without PL=MUF–concentration of the wells without test substance and without PL The $IC_{50}$ is calculated from the inhibition of the PL [%] in a series of dilutions of tested samples. This is the concentration, at which the activity of the PL is 50% inhibited.

TABLE 4.1

Inhibition of the PL by the individual substances
(mean values of at least 2 independent tests)

| Test Substance | $IC_{50}$ (ppm) |
|---|---|
| 3-methoxypterocarpan | 350 |
| Medicarpin | 425 |
| Maackiain | 147 |
| Pao rosa heartwood extract | 80 |

The results of the inhibition of the PL are used as a preliminary test and are confirmed on LPL. To obtain LPL, 3T3-L1 cells (mouse embryonal fibroblast adipocyte cell line) are seeded in a 6-well plate with collagen I-coating in a concentration of $3 \times 10^5$ cells/well. The cultivation and differentiation of the cells takes place analogously to the details in Example 2 (adipogenesis assay). During the differentiation LPL, is increasingly expressed. The LPL is present in a membrane-bound state and is released by one hour incubation with heparin solution at 2-8° C. in the supernatant of the cells.

The LPL thus obtained, in the presence of test substances in different use concentrations, has methylumbelliferyl oleate (MUF oleate) added as the substrate. Fluorescent methylumbelliferyl (MUF) is produced by hydrolysis of the MUF oleate by LPL and is quantified. The inhibition of the hydrolysis of the MUF oleate is a measure of the inhibition of the activity of the LPL and therefore the lipogenesis.

$$\text{Inhibition of the LP [\%]} = 100 - \left( \frac{MUF \text{ test substance} - MUF \text{ control without } LPL}{MUF \text{ control} - MUF \text{ control without } LPL} \times 100 \right)$$

wherein

MUF test substance=MUF–concentration of the wells with test substance and with LPL MUF control=MUF–concentration of the wells without test substance, but with LPL MUF control without LPL=MUF–concentration of the wells without test substance and without LPL The $IC_{50}$ is calculated from the inhibition of the LPL [%] in a series of dilutions of tested samples. This is the concentration at which the activity of the LPL and therefore the lipogenesis is 50% inhibited.

TABLE 4.2

Inhibition of the LPL by the individual substances
(mean values of at least 2 independent tests)

| Test Substance | $IC_{50}$ (ppm) |
|---|---|
| 3-methoxypterocarpan | 67.0 |
| Medicarpin | 788 |
| Maackiain | 104.2 |
| Pao rosa heartwood extract | 41.5 |

EXAMPLE 5

Lipolysis Assay (In Vitro)

Primary human subcutaneous preadipocytes (Lonza) are seeded in a 96-well microtiter plate at a concentration of $1 \times 10^4$ cells/well. Until confluence is reached, cultivation takes place at 37° C. and 5% $CO_2$ in DMEM, enriched with 10% foetal calf serum. To induce the differentiation of preadipocytes to adipocytes there follows the addition DMEM enriched with 10% foetal calf serum, with added 10 μg/ml insulin, 1 μM dexamethasone and 1 mM IBMX (3-isobutyl-1-methylxanthine). A cultivation for 14 to 20 days follows. During this time, the medium can optionally be replaced by DMEM, enriched with 10% foetal calf serum.

Various concentrations of the test substances are applied to the cells in DMEM, with bovine serum albumen added. After about 20 hours of incubation, the quantification takes place of free glycerol in the supernatant of the cells, which is discharged therefrom after hydrolysis of triglycerides in the cells and is a measure of the lipolysis of the cells. The quantification of the free glycerol is carried out based on an enzymatic method with a free glycerol reagent.

The stimulation of the lipolysis in the presence of test substances is calculated according to the following equation:

$$\text{Stimulation of the lipolysis } [\%] = \left( \frac{\text{A test substance} - \text{A test substance without cells}}{\text{A control} - \text{A control without cells}} \times 100 \right) - 100$$

wherein

A test substance=absorption of the wells with test substance and with cells

A test substance without cells=absorption of the wells with test substance without cells (absorption control)

A control=absorption of the wells without test substance, but with cells

A control without cells=absorption of the wells without test substance and without cells The $IC_{50}$ is calculated from the lipolysis stimulation [%] in a series of dilutions of tested samples. This is the concentration at which the lipolysis is 50% stimulated.

TABLE 5.1

Activity by the individual substances based on the lipolysis (mean values from at least 2 independent tests). The tested substances show no activity with regard to lipolysis at the maximum use concentrations listed, in other words the lipolysis is neither inhibited nor stimulated by the test substances.

| Test Substance | Activity (max. use concentration (ppm)) |
|---|---|
| 3-methoxypterocarpan | No activity (25 ppm) |
| Medicarpin | No activity (25 ppm) |
| Maackiain | No activity (25 ppm) |
| Pao rosa heartwood extract | No activity (10 ppm) |

The inhibition of the lipolysis in the presence of test substances is calculated according to the following equation:

$$\text{Inhibition of the lipolysis } [\%] = 100 - \left( \frac{\text{A test substance} - \text{A test substance without cells}}{\text{A control} - \text{A control without cells}} \times 100 \right)$$

wherein

A test substance=absorption of the wells with test substance and with cells

A test substance without cells=absorption of the wells with test substance without cells (absorption control)

A control=absorption of the wells without test substance, but with cells

A control without cells=absorption of the wells without test substance and without cells The $IC_{50}$ is calculated from the lipolysis inhibition [%] in a series of dilutions of tested samples. This is the concentration at which the lipolysis is 50% inhibited.

TABLE 5.2

Inhibition of the lipolysis by the individual substances
(mean values of at least 2 independent tests)

| Test Substance | $IC_{50}$ (ppm) |
|---|---|
| Santal (isolated from the heartwood extract of red sandalwood (Pterocarpus santalinus)) | 1.92 ppm |
| Formononetin (company Phytolab) | 53.7 ppm |

EXAMPLE 6

The effectivity of preparations according to the invention was tested on 30 women (Caucasian type). Each of the test subjects treated one leg for two months with a preparation according to the invention as given below and treated the other leg with a pterocarpan-free control preparation. After two months a test panel of 3 trained examiners assessed the improvement in the cellulite appearance using a scale of 1 (just perceivable improvement) to 5 (complete elimination of the cellulite pattern). On average an improvement of around 2 was achieved.

| | Ingredient | INCI-designation | % by weight |
|---|---|---|---|
| A | Dracorin GOC | Glyceryl Oleate Citrate, Caprylic/Capric Triglyceride | 2.0 |
| | Neutral oil | Caprylic/Capric Triglyceride | 4.0 |

-continued

| Ingredient | INCI-designation | % by weight |
|---|---|---|
| Paraffin oil | Paraffinum Liquidum | 4.0 |
| PCI-Liquid 100 | Cetearyl Ethylhexanoate | 7.0 |
| Dragoxat 89 | Ethylhexyl Isononanoate | 3.0 |
| Dow Corning 345 Fluid | Cyclomethicone | 0.5 |
| Dragosantol 100 | Bisabolol | 0.1 |
| B Water | Water (Aqua) | 73.7 |
| Pemulen TR2 | Acrylates/C10-30 Alkyl Acrylate Crosspolymer | 0.2 |
| C Hydrolite-5 | Pentylene Glycol | 5.0 |
| 3-Methoxypterocarpan (Compound B) | | 0.1 |
| D Sodium Hydroxide 10% ige solution | Sodium Hydroxide | 0.4 |

Production:

Allow Pemulen TR2 to swell in water and predissolve 3-methoxypterocarpan in hydrolite-5. Mix phase A. Add phase C to phase A then add phase B to phase NC and emulsify with the Homorex. Continue to stir the O/W with the paddle mixer and in the process add phase D.

FORMULATION EXAMPLES

| Ingredient | INCI-Name | 1 | 2 | 3 | 4 | 5 | 6 | 7 | 8 | 9 | 10 |
|---|---|---|---|---|---|---|---|---|---|---|---|
| 3-methoxypterocarpan (B) or | | 0.1 | 0.02 | 0.05 | 0.08 | 0.02 | 0.1 | 0.08 | 0.05 | 0.1 | 0.1 |
| Pao rosa heartwood extract | | 0.2 | 0.02 | 0.1 | 0.16 | 0.04 | 0.2 | 0.16 | 0.1 | 0.2 | 0.2 |
| A-C Polyethylene 9 A | Polyethylene | | | | | | | 5 | | | |
| Actipone Black Coffee GW | Water (Aqua), Glycerin, Coffea Arabica (Coffee) Seed Extract, Coffea Robusta Seed Extract | | | | 1 | | | | | | |
| Actipone Laminaria Saccharina | Glycerin, Water (Aqua), Laminaria Saccharina Extract | | | | | | | | | 0.5 | |
| Actipone Nutgrass (Motha) Root GW | Water (Aqua), Glycerin, Cyperus Rotundus Root Extract | | | | | | 1 | | | | |
| Aristoflex AVC | Ammonium Acryloyldimethyltaurate/VP Copolymer | | | | | | 0.7 | | | | |
| Avocado oil | Persea Gratissima (Avocado) Oil | | | 2 | | 6 | | | | | |
| Biotive Esculin Sesquihydrate | Esculin | | | | | | | | | | 0.3 |
| (−)-alpha-Bisabolol natural | Bisabolol | | | | | | | | 0.1 | | |
| Butylene glycol-1,3 | Butylene Glycol | | | | | | | | | 14.34 | 5 |
| Carbopol Ultrez-10 | Carbomer | | | | 0.3 | | | | | | |
| Carbopol Ultrez 21 | Acrylates/C10-30 Alkyl Acrylate Crosspolymer | | | | | 0.2 | | | | | |
| Carnitine | Carnitine | | | | | | | | 0.8 | | 0.5 |
| Cetiol SB 45 | Butyrospermum Parkii (Shea Butter) | | | | 2 | | | | | | |
| Citric acid sln. 10% | Citric Acid | 0.3 | | | | | | 0.05 | 0.2 | | |
| Comperlan 100 | Cocamide MEA | 0.5 | | | | | | | | | |
| Covi-Ox T-70 | Tocopherol | | | 0.2 | | 0.1 | 0.1 | | | | |
| Cutina GMS-V | Glyceryl Stearate | | | | 1 | | | | | | |
| D-Panthenol | Panthenol | | | | | | | | 0.5 | | |
| Dow Corning 200(100cs) Silicone Fluid | Dimethicone | | | | | | | | 3 | | |
| Dow Corning 246 Fluid | Cyclohexasiloxane | | | | | 2 | | | | | |
| Dow Corning 345 Fluid | Cyclomethicone | | | 0.5 | | | | | | | |
| Dracorin 100 S.E.P. | Glyceryl Stearate, PEG-100 Stearate | | | | | | | 7 | | | |
| Dracorin CE | Glyceryl Stearate Citrate | | | | 3 | | | | | | |
| Dracorin GOC | Glyceryl Oleate Citrate, Caprylic/Capric Triglyceride | | | 2 | | | | | | | |
| Drago-Oat-Active | Water (Aqua), Butylene Glycol, Avena Sativa (Oat) Kernel Extract | | | | 1 | | | | | | |

| Ingredient | INCI | | | | | | | | |
|---|---|---|---|---|---|---|---|---|---|
| Dragocid Liquid | Phenoxyethanol, Methylparaben, Ethylparaben, Butylparaben, Propylparaben, Isobutylparaben | | | | 0.8 | 0.8 | | 0.4 | 0.8 |
| Dragoderm | Glycerin, *Triticum Vulgare* (Wheat) Gluten, Water (Aqua) | 1 | | | | | | | |
| Dragosantol 100 | Bisabolol | | | 0.1 | | 0.1 | 0.5 | | |
| Dragosine | Carnosine | | | | | | 0.05 | | |
| Dragoxat 89 | Ethylhexyl Isononanoate | | 10 | 3 | | 4 | 5 | | |
| Edeta B Powder | Tetrasodium EDTA | | | | | | | 0.1 | |
| Edeta BD | Disodium EDTA | 0.1 | | | | | | | |
| Emulgin B2 | Ceteareth-20 | | | | | | | 2 | |
| Emulsiphos | Potassium Cetyl Phosphate, Hydrogenated Palm Glycerides | | | | | 1.2 | | | 1 |
| Ethanol 96% ig | Alcohol Denat. | | | | | | | | 10 |
| Essential oil | Essential Oil | | | | | | 1 | | |
| Extrapone Butcher's broom GW P | Glycerin, Water (Aqua), Pentylene Glycol, *Ruscus Aculeatus* Root Extract | | | | | | | 1 | |
| Extrapone *Ginkgo Biloba* | Propylene Glycol, Water (Aqua), *Ginkgo Biloba* Leaf Extract, Glucose, Lactic Acid | | | 1 | | | | | |
| Extrapone Green Tea (Organic) GW | Water (Aqua), Glycerin, *Camellia Sinensis* Leaf Extract | | | | | | | 2 | |
| Extrapone *Guarana* | Water (Aqua), Propylene Glycol, *Paullinia Cupana* Seed Extract, Alcohol | 1 | | | | | | | |
| Extrapone Horse Chestnut | Propylene Glycol, Water (Aqua), *Aesculus Hippocastanum* (Horse Chestnut) Seed Extract, Glucose, Lactic Acid | | | | | | | | 1 |
| Extrapone Ivy | Propylene Glycol, Water (Aqua), *Hedera Helix* (Ivy) Leaf/Stem Extract, Glucose, Lactic Acid | | | | | | 1 | | |
| Extrapone Orange Flower | Water (Aqua), Propylene Glycol, *Citrus Aurantium Amara* (Bitter Orange) Flower Extract | | | | | | 3 | | 1 |
| Extrapone Orange Peel | Water (Aqua), Propylene Glycol, Alcohol, Citrus *Aurantium Dulcis* (Orange) Peel Extract | | | | | | | 1 | |
| Extrapone Seaweed | Water (Aqua), Butylene Glycol, *Fucus Vesiculosus* Extract | | | | | | | 2.5 | |
| Frescolat MGA | Menthone Glycerin Acetal | | | 0.5 | | | | | |
| Frescolat ML | Menthyl Lactate | | | | | | | 0.5 | |
| Genapol LRO Liquid | Sodium Laureth Sulfate | 37 | | | | | | | |
| Glycerin | Glycerin | | | | 3 | 3 | | 4 | 3 |
| Hydrolite 5 | Pentylene Glycol | | | 5 | | 5 | 5 | | 3 |
| Hydroviton | Water (Aqua), Glycerin, Sodium Lactate, Lactic Acid, TEA-Lactate, Serine, Urea, Sorbitol, Sodium Chloride, Allantoin | | | 1 | | | | | |
| Isodragol | Triisononanoin | | 13 | | 4 | | | | |
| Isopropyl-palmitate | Isopropyl-Palmitate | | | | | | 3 | | |
| Jojoba Oil Ethoxilate (Oxypon 328) | Peg-26 Jojoba Acid, Peg-26 Jojoba Alcohol | | | | | | | 1 | |
| Cocoa butter, pulverised | *Theobroma Cacao* (Cocoa) Seed Butter | | | | | 0.7 | | | |
| Potassium sorbate | Potassium Sorbate | | | | 0.2 | | | | |
| Karion F | Sorbitol | | | | | | | 1 | |
| Keltrol CG-RD | Xanthan Gum | | | 0.1 | 0.2 | | | | |
| Caffeine purest | Caffeine | | | | | | | 0.5 | 0.2 |
| Lanette 16 | Cetyl Alcohol | | | | 2.5 | | 3 | | |
| Lanette O | Cetearyl Alcohol | | | | | 1.5 | | | |

| | | | | | | | | | | |
|---|---|---|---|---|---|---|---|---|---|---|
| Solubilizer | PEG-40 Hydrogenated Castor Oil, Trideceth-9, Water (Aqua) | | | | | | | | | 0.5 |
| *Macadamia* nut oil | *Macadamia Ternifoia* Seed Oil | | 0.5 | 3 | | | | | | |
| Sea salt (Dead Sea) | Sea Salt (Maris Sal) | | | | | | | 1.5 | | |
| Merquat 550 | Polyquaternium-7 | 0.5 | | | | | | | | |
| Sodium benzoate | Sodium Benzoate | 0.5 | | | | | | | | |
| Sodium chloride | Sodium Chloride | 1 | | | | | | | | |
| Sodium hydroxide solution 10% | Sodium Hydroxide | | | 0.4 | 0.45 | 0.6 | 0.01 | | | 0.4 |
| Sodium stearate | Sodium Stearate | | | | | | | 9 | | |
| Neo Actipone White Tea | *Camellia Sinensis* Leaf Extract | | | 3 | | 1 | | | | |
| Neo Heliopan BB | Benzophenone-3 | | | | 0.1 | | 0.1 | | | |
| Neutral oil | Caprylic/Capric Triglyceride | | | 4 | | | | 10 | | |
| Orange blossom extract | *Citrus Aurantium Amara* (Bitter Orange) Flower Extract | 1 | | 1 | | | | | | |
| Oxynex K Liquid | PEG-8, Tocopherol, Ascorbyl Palmitate, Ascorbic Acid, Citric Acid | | | | | | | 0.1 | | |
| Paraffin oil | Paraffinum Liquidum | | 49.6 | 4 | | | | | | |
| Perfume oil | Fragrance | 0.5 | 0.5 | 0.2 | 0.3 | 0.3 | | 0.4 | 0.4 | 0.2 |
| PCL-Liquid 100 | Cetearyl Ethylhexanoate | | 21 | 7 | 3 | 3 | 3 | | | |
| PCL-Solid | Stearyl Heptanoate, Stearyl Caprylate | | | | | 1.5 | 1.5 | | | |
| Pemulen TR-2 | Acrylates/C10-30 Alkyl Acrylate Crosspolymer | | | 0.2 | | | | | | |
| Phytoconcentrole Shea Butter | *Glycine Soya* (Soybean) Oil, *Butyrospermum Parkii* (Shea Butter) | | 0.5 | | | | | | | |
| Propylenglycol-1,2 | Propylene Glycol | | | | | | | | 2 | |
| RonaCare Nicotinamide | Niacinamide | | | | | 0.1 | | | | |
| Sepigel 305 | Polyacrylamide, C 13-14 Isoparaffin, Laureth-7 | | | | | | | | 2 | |
| Stabileze QM | PVM/Ma Decadiene Crosspolymer | | | | | | | | | 0.25 |
| SymCalmin | Butylene Glycol, Pentylene Glycol, Hydroxyphenyl Propamidobenzoic Acid | | | | | 1 | | | | |
| Symdiol 68 | 1,2-Hexanediol, Caprylyl Glycol | | 1 | | | | | | | |
| SymGlucan | Water (Aqua), Glycerin, Beta-Glucan | | | | | 1 | | | | |
| SymMatrix | Maltodextrin, *Rubus Fruticosus* (Blackberry) Leaf Extract | | | | | 0.5 | | | | |
| SymMollient W/S | Trideceth-9, PEG-5 Isononanoate, Water (Aqua) | 1 | | | | | | | | |
| SymPeptide 222 | Glycerin, Water (Aqua), Myristoyl Pentapeptide-8 | | | | | | | 5 | | |
| SymRelief | Bisabolol, *Zingiber Officinale* (Ginger) Root Extract | | 0.1 | | | | | | | |
| SymRepair | Hexyldecanol, Bisabolol, Cetylhydroxyproline Palmitamide, Stearic Acid, *Brassica Campestris* (Rapeseed) Sterols | | 1 | | | | | | | |
| SymVital | *Aloe Barbadensis* Leaf Juice Powder, Magnesium Ascorbyl Phosphate, *Rubus Idaeus* (Raspberry) Leaf Extract | | | | | | | 0.5 | | |

| | | | | | | | | | |
|---|---|---|---|---|---|---|---|---|---|
| Talc | Talc | | | | | | | 3 | |
| Tego Betain L7 non preserved | Cocamidopropyl Betain | 6 | | | | | | | |
| Vitamin A Palmitate | Retinyl Palmitate | | 0.05 | | | | | | |
| Vitamin E Acetate | Tocopheryl Acetate | | 0.5 | | 0.5 | | | | |
| Water | Water (Aqua) | to 100 | to 100 | to 100 | to 100 | to 100 | to 100 | to 100 | to 100 |

| Example No. | Product Form |
|---|---|
| 1 | Shower bath |
| 2 | Anti-cellulite body oil |
| 3 | Body spray O/W |
| 4 | Cream O/W |
| 5 | Body lotion O/W |
| 6 | Anti-cellulite gel |
| 7 | Body exfoliant |
| 8 | Anti-cellulite balm |
| 9 | Moisture stick |
| 10 | Anti-cellulite spray gel |

EXAMPLES

F1-F10: Orally Consumable Use Examples ["Beauty from Inside"]

Example F1

Fruit Gums

| | % by weight |
|---|---|
| Water | to 100 |
| Saccharose | 34.50 |
| Glucose syrup, DE 40 | 31.89 |
| Iso Syrup C* Tru Sweet 01750 (Cerestar GmbH) | 1.50 |
| Gelatin 240 Bloom | 8.20 |
| Yellow and red food colourants | 0.01 |
| Citric acid | 0.20 |
| 3-methoxypterocarpan (B) | 0.075 |

Example F2

Hard Boiled Candy

| | I (% by weight) | II (% by weight) |
|---|---|---|
| Sugar (Saccharose) | to 100 | to 100 |
| High fructose corn syrup | 41.00 | 41.00 |
| Maltose | 3.00 | 3.00 |
| Palm kernel oil | 0.90 | 0.90 |
| Citric acid | 0.30 | 0.30 |
| Ginger extract | 0.40 | — |
| Ginseng extract | — | 0.40 |
| Blue colourant | 0.01 | 0.01 |
| 3-methoxypterocarpan (B) | 0.10 | — |
| Pao rosa heartwood extract | — | 0.16 |
| Honey | — | 1.50 |
| Honey flavour | — | 0.30 |

Example F3

Gelatin Capsules Suitable for Direct Consumption

| | % by weight | | |
|---|---|---|---|
| | I | II | III |
| Gelatin covering: | | | |
| Glycerin | 2.014 | 2.014 | 2.014 |
| Gelatin 240 Bloom | 7.91 | 7.91 | 7.91 |
| Aspartame | 0.05 | — | — |
| Sucralose | 0.035 | 0.050 | 0.070 |
| Allura Red (red colourant) | 0.006 | 0.006 | 0.006 |
| Brilliant Blue (blue colourant) | 0.005 | 0.005 | 0.005 |
| Core composition: | | | |
| Plant oil triglyceride (coconut oil fraction) | to 100 | to 100 | to 100 |
| Flavour G | 9.95 | 12.0 | 12.0 |
| 3-methoxypterocarpan (Compound (B)) | 0.07 | 0.10 | — |
| Pao rosa heartwood extract | — | — | 0.20 |

Flavour G had the following composition here (details in % by weight in each case): 0.1% neotam powder, 29.3% peppermint oil arvensis, 29.35% peppermint piperta oil Willamette, 2.97% sucralose, 2.28% triacetin, 5.4% diethyl tartrate, 12.1% peppermint oil yakima, 0.7% ethanol, 3.36% 2-hydroxyethylmenthylcarbonate, 3.0% 2-hydroxypropylmenthylcarbonate, 5.77% D-limonene, 5.67% L-menthylacetate.

The gelatin capsules I, II, III suitable for direct consumption were produced according to WO 2004/050069 and in each case had a diameter of 5 mm and the weight ratio of the core material to the covering material was 90:10. The capsules in each case opened in the mouth within less than 10 seconds and dissolved completely within less than 50 seconds.

Example F4

Tablets in Round Tablet Form

|  | % by weight | | |
|---|---|---|---|
|  | I | II | III |
| Magnesium stearate | 0.9 | 0.9 | 0.9 |
| Citric acid | 0.2 | 0.2 | 0.2 |
| 3-methoxypterocarpan (B) | 0.05 | 0.10 | — |
| Pao rosa heartwood extract | — | — | 0.23 |
| Dextrose | to 100 | to 100 | to 100 |

Example F5

Chewing Gum (with Sugar and Sugar-Free)

|  | % by weight | |
|---|---|---|
|  | I | II |
| Chewing gum base | 21.0 | 30.0 |
| Glycerin | 0.5 | 1.0 |
| Menthol spearmint *eucalyptus* flavour P1 | 1.0 | 1.4 |
| Glucose syrup | 16.5 | — |
| Powder sugar | to 100 | — |
| 3-methoxypterocarpan (compound (B)) | 0.15 | 0.20 |
| Sorbitol (in powder form) | — | to 100 |
| Palatinit |  | 9.5 |
| Xylitol |  | 2.0 |
| Mannitol |  | 3.0 |
| Aspartame |  | 0.1 |
| Acesulfame K |  | 0.1 |
| Emulgum (emulsifier) |  | 0.3 |
| Sorbitol 70%, in water |  | 14.0 |

Flavour P1 had the following composition (details in % by weight in each case):

0.05% isobutyraldehyde, 0.05% 3-octanol, 0.05% dimethylsulfide, 0.1% trans-2-hexanal, 0.1% cis-3-hexanol, 0.1% natural 4-terpineol, 0.1% isopulegol, 0.2% natural piperiton, 0.3% linalool, 1.0% isoamylalcohol, 1.0% isovaleraldehyde, 2.5% natural alpha-pinene, 2.5% natural beta-pinene, 8.0% eucalyptol, 7.0% 1-menthylacetate, 12.0% 1-menthone, 5.0% isomenthone, 20.5% l-carvone, 39.45% l-menthol.

The following table relates to Examples F6-F10:
Example F6=Instant drink powder
Example F7=Instant drink powder, sugar-free
Example F8=Carbonated lemonade (soft drink)
Example F9=Soya fruit drink
Example F10=Reduced-fat yoghourt

|  | % by weight | | | | |
|---|---|---|---|---|---|
|  | F6 | F7 | F8* | F9 | F10 |
| 3-methoxypterocarpan (B) | 0.50 | 0.90 | 0.05 | 0.05 | 0.10 |

|  | % by weight | | | | |
|---|---|---|---|---|---|
|  | F6 | F7 | F8* | F9 | F10 |
| *Pao rosa* heartwood extract | — | — | — | 0.08 | — |
| Sugar (Saccharose) | to 100 |  |  |  |  |
| Citric acid | 4.00 | 33.33 | 0.2 |  |  |
| Trisodiumcitrate | 0.26 |  |  |  |  |
| Tricalciumphosphate | 0.22 |  |  |  |  |
| Ascorbic acid (Vitamin C) | 0.24 | 0.44 |  |  |  |
| Opacifier and Titanium dioxide (E 171) | 0.20 |  |  |  |  |
| Xanthan gum (E 415) | 0.072 |  |  |  |  |
| Sodiumcarboxy-methyl cellulose (E 467) | 0.064 |  |  |  |  |
| Pectin (E 440) | 0.04 |  |  |  |  |
| Spray-dried pineapple flavour, contains yellow colourant tartrazine | 0.40 |  |  |  |  |
| Spray-dried raspberry flavour, contains red colourant |  | 11.50 |  |  |  |
| Lemon-lime flavour |  |  | 0.01 |  |  |
| D-Limonene |  |  | 0.005 |  |  |
| Maltodextrin (powder) |  | to 100 |  |  |  |
| Aspartame |  | 3.30 |  |  |  |
| Saccharose |  |  | 8.0 | 6.0 | 5.0 |
| Hesperetin (1% by weight in 1,2-propyleneglycol) |  |  | 0.05 |  |  |
| Ethylhydroxymethyl furanone |  |  | 0.01 ppb |  |  |
| Vanilla flavour |  |  |  | 0.10 | 0.125 |
| Vanillin |  |  | 15 ppb |  |  |
| Maltol |  |  | 350 ppb |  |  |
| 2,5-dimethyl-4-hydroxy-2H-furan-3-one |  |  | 3 ppb |  |  |
| 1,2-propyleneglycol |  |  | 0.1 |  |  |
| Mixture of fruit juice concentrates |  |  |  | 45.0 |  |
| Soya powder |  |  |  | 5.0 |  |
| Yoghurt (1.5% by weight fat) |  |  |  |  | to 100 |
| Water |  |  | to 100 | to 100 |  |

*Carbon dioxide is added after pouring into bottles.

The invention claimed is:

1. A cosmetic, dermatological, or pharmaceutical composition comprising:
   (a) a *Pao Rosa* extract that has been treated with activated carbon comprising one or more compounds of formula (I),

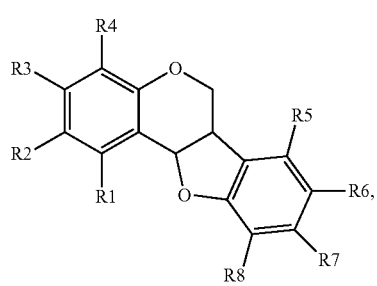

wherein the radicals R1 to R8, independently of one another, are hydrogen, hydroxy or C1-C4-alkoxy, and/or two adjacent radicals together form a methylenedioxy group, and wherein the total amount of the one or more compounds of formula (I) accounts for 0.001-1 wt. % of the composition, based on the total weight of the composition; and (b) 0.005-10 wt. %, based on the total weight of the composition, of a lipolysis stimulant of formula (Xa),

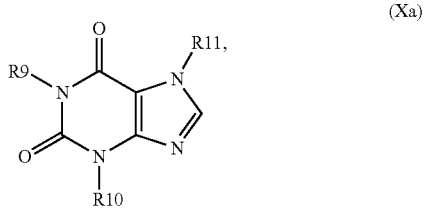

(Xa)

wherein R9, R10 and R11, independently of one another, is hydrogen or methyl.

2. The composition according to claim 1, wherein the radicals R1 to R8, independently of one another, are hydrogen, hydroxy, methoxy or ethoxy, and optionally one or more pairs of adjacent radicals in each case together form a methylenedioxy group.

3. The composition according to claim 1, wherein at least one compound of formula (I) is a compound of formula (IA),

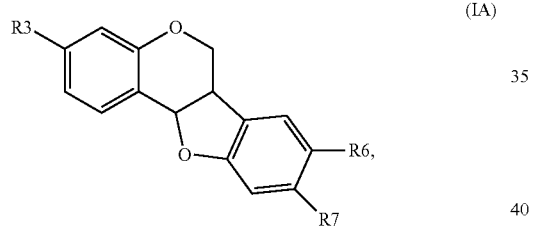

(IA)

wherein the radical R3 is hydrogen, hydroxy or methoxy, and the radicals R6 and R7 together form a methylenedioxy group or, independently of one another, are hydrogen, hydroxy or methoxy.

4. The composition according to claim 1, wherein the *Pao Rosa* extract comprises di-hydroxy-dimethoxy isoflavone, di-hydroxy-trimethoxy isoflavone, isoflavone, 2',7-dihydroxy-4',6-dimethoxyisoflavone, afrormosin, maackiain, and medicarpin.

5. The composition according to claim 1, wherein the *Pao Rosa* extract comprises not more than 16% by weight of methoxylated isoflavones, based on the total dry mass of the *Pao Rosa* extract.

6. The composition according to claim 1 having photo-irritation factor of less than 5.

7. The composition according to claim 1, wherein the total amount of *Pao Rosa* extract accounts for 0.001-5 wt. % of the composition, based on the total weight of the composition.

8. A cosmetic, dermatological, or pharmaceutical composition comprising:

(a) a compound of formula (B),

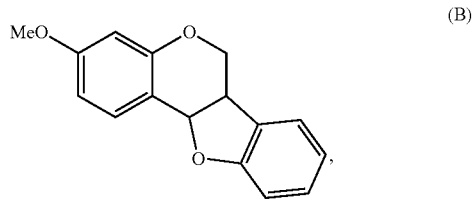

(B)

and (b) 0.005-10 wt. %, based on the total weight of the composition, of a lipolysis stimulant of formula (Xa),

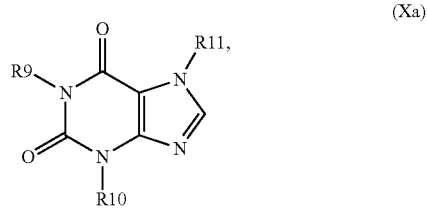

(Xa)

wherein R9, R10 and R11, independently of one another, is hydrogen or methyl.

* * * * *